US012270113B2

(12) United States Patent
Mohri et al.

(10) Patent No.: US 12,270,113 B2
(45) Date of Patent: Apr. 8, 2025

(54) FUEL PRODUCING SYSTEM

(71) Applicant: HONDA MOTOR CO., LTD., Tokyo (JP)

(72) Inventors: Masahiro Mohri, Saitama (JP); Kazuki Yanagisawa, Saitama (JP); Misato Maki, Saitama (JP)

(73) Assignee: HONDA MOTOR CO., LTD., Tokyo (JP)

(*) Notice: Subject to any disclaimer, the term of this patent is extended or adjusted under 35 U.S.C. 154(b) by 366 days.

(21) Appl. No.: 17/680,322

(22) Filed: Feb. 25, 2022

(65) Prior Publication Data

US 2022/0316077 A1    Oct. 6, 2022

(30) Foreign Application Priority Data

Mar. 31, 2021   (JP) .................. 2021-060700

(51) Int. Cl.
| C25B 1/042 | (2021.01) |
| C07C 1/04 | (2006.01) |
| C25B 1/23 | (2021.01) |
| C25B 15/08 | (2006.01) |

(52) U.S. Cl.
CPC ............ C25B 1/042 (2021.01); C07C 1/0425 (2013.01); C25B 1/23 (2021.01); C25B 15/087 (2021.01)

(58) Field of Classification Search
None
See application file for complete search history.

(56) References Cited

U.S. PATENT DOCUMENTS

| 2016/0053388 A1 | 2/2016 | Reytier et al. |
| 2019/0194816 A1 | 6/2019 | Brunot et al. |
| 2020/0165732 A1* | 5/2020 | Peschel ............... C01B 32/40 |
| 2023/0114967 A1* | 4/2023 | Echigo ................ C25B 15/081 |
| | | 518/704 |

FOREIGN PATENT DOCUMENTS

| CN | 110730830 A | 1/2020 |
| JP | 2013119556 A | 6/2013 |
| JP | 2014152219 A | 8/2014 |
| JP | 2016522166 A | 7/2016 |
| JP | 2019112717 A | 7/2019 |
| JP | 2020525641 A | 8/2020 |
| WO | WO-2020203087 A1 * | 10/2020 |

OTHER PUBLICATIONS

Office Action issued in the CN Patent Application No. 202210183848.7, mailed on Jul. 10, 2023.
Zhou Anning et al., "Clean Coal Technology", China University of Mining and Technology Press, p. 308, 2nd edition, 20180228.
Decision of Refusal issued Sep. 30, 2024 in the CN Patent Application No. 202210183848.7.

* cited by examiner

Primary Examiner — Louis J Rufo
(74) Attorney, Agent, or Firm — CKC & Partners Co. LLC

(57) ABSTRACT

A fuel producing system includes an electrolyzer that is supplied with a raw material gas containing carbon dioxide and water vapor, and electrolyzes the raw material gas to generate a product gas containing hydrogen and carbon monoxide, and a first gas-liquid separator that performs gas-liquid separation on the product gas generated in the electrolyzer. Water vapor produced from water separated in the first gas-liquid separator or water vapor produced from water from a water supply source is allowed to be supplied to the electrolyzer in addition to the raw material gas.

5 Claims, 6 Drawing Sheets

FUEL PRODUCING SYSTEM

This application is based on and claims the benefit of priority from Japanese Patent Application No. 2021-060700, filed on 31 Mar. 2021, the content of which is incorporated herein by reference.

BACKGROUND OF THE INVENTION

Field of the Invention

The present invention relates to a fuel producing system.

Related Art

The following Patent Document 1 discloses a fuel producing apparatus for producing fuel such as methane using water and carbon dioxide. This fuel producing apparatus manufactures fuel by using an electrolyzing unit having an oxygen ion permeable membrane between an anode electrode and a cathode electrode, and a synthesizing unit which is provided with a catalyst so as to synthesize the fuel. Specifically, first, water is vaporized into water vapor, and the water vapor and carbon dioxide are adjusted to have a predetermined molar ratio, and then supplied to a cathode electrode side of the electrolyzing unit. Power is applied between the anode electrode and the cathode electrode, whereby the water vapor and carbon dioxide supplied to the cathode electrode side are sequentially electrolyzed, and hydrogen and carbon monoxide are generated on the cathode electrode side of the electrolyzing unit. The generated hydrogen and carbon monoxide are cooled and pressurized, and then passed through the catalyst in the synthesizing unit. As a result, a fuel composed of hydrogen and carbon monoxide is produced.

Patent Document 1: Japanese Unexamined Patent Application, Publication No. 2013-119556

SUMMARY OF THE INVENTION

Conventionally, water and carbon dioxide discharged from garbage disposal facilities and the like have been used as water and carbon dioxide to be used as raw materials for producing fuel. In the garbage disposal facilities and the like, the amount ratio of water to carbon dioxide is not constant in the discharged water and carbon dioxide.

Therefore, there is a risk that water vapor out of water vapor and carbon dioxide to be supplied to the electrolyzing unit may be short in supply.

Further, conventionally, since a gas composed of hydrogen and carbon monoxide generated in the electrolyzing unit contains water, the gas is subjected to gas-liquid separation by a gas-liquid separator. The water separated in the gas-liquid separator is discarded without being particularly used. At this time, the separated water is subjected to a pH treatment and the like so as to meet the waste water quality standards. As described above, conventionally, not only water has been wasted, but also the treatment cost for water has been high.

The present invention has an object to provide a fuel producing system that can solve the shortage of water vapor as a raw material and can reduce water waste.

(1) An embodiment of the present invention includes: an electrolyzer (electrolyzing unit) that is supplied with a raw material gas containing carbon dioxide and water vapor, and electrolyzes the raw material gas to generate a product gas containing hydrogen and carbon monoxide; and a first gas-liquid separator (first gas-liquid separation unit) that performs gas-liquid separation on the product gas generated in the electrolyzer. Water vapor produced from water separated in the first gas-liquid separator or water vapor produced from water from a water supply source is allowed to be supplied to the electrolyzer in addition to the raw material gas. Typically, the electrolyzing unit is a co-electrolyzing unit.

(2) An embodiment of the present invention described above in (1) may further include: a synthesizer (synthesizing unit) that generates a synthesis gas by passing, through a catalyst, the product gas from which water has been separated in the first gas-liquid separator, the synthesis gas containing methane; and a second gas-liquid separator (second gas-liquid separation unit) that performs gas-liquid separation on the synthesis gas generated in the synthesizer. In addition to the raw material gas, water vapor produced from water separated in the first gas-liquid separator and water vapor produced from water separated in the second gas-liquid separator, or water vapor produced from water from the water supply source may be allowed to be supplied to the electrolyzer.

(3) According to an embodiment of the present invention described above in (2), when an outside air temperature is equal to or higher than a predetermined temperature, a first operation may be performed in which water vapor produced from water from the water supply source is supplied to the electrolyzer in addition to the raw material gas. When the outside air temperature is lower than the predetermined temperature, a second operation may be performed in which water vapor produced from water separated in the first gas-liquid separator and water vapor produced from water separated in the second gas-liquid separator are supplied to the electrolyzer in addition to the raw material gas.

(4) According to an embodiment of the present invention described above in (3), when a deviation from a set value of a molar ratio of water vapor/carbon dioxide in the raw material gas becomes equal to or less than a predetermined value during the second operation, a third operation may be performed in which in addition to the raw material gas, water vapor produced from water separated in the first gas-liquid separator and water vapor produced from water separated in the second gas-liquid separator, water vapor produced from water from the water supply source is supplied to the electrolyzer.

(5) According to an embodiment of the present invention described above in (4), when a water level in a first drain tank in which water separated in the first gas-liquid separator is stored, and a water level in a second drain tank in which water separated in the second gas-liquid separator is stored are lower than a set water level during the third operation, water vapor produced from water from the water supply source may be supplied to the electrolyzer in addition to the raw material gas, and supply of water vapor produced from water separated in the first gas-liquid separator and water vapor produced from water separated in the second gas-liquid separator may be stopped.

(6) According to an embodiment of the present invention described above in (3), when a deviation from a set value of a molar ratio of water vapor/carbon dioxide in the raw material gas becomes equal to or less than a predetermined value during the first operation, a fourth operation may be performed in which in addition to the raw material gas and water vapor produced from water from the water supply source, water vapor produced from water separated in the first gas-liquid separator and water vapor produced from water separated in the second gas-liquid separator are supplied to the electrolyzer.

According to the present invention, it is possible to provide a fuel producing system that can solve the shortage of water vapor as a raw material and does not waste water.

DETAILED DESCRIPTION OF THE INVENTION

Hereinafter, a specific embodiment of the present invention will be described in detail with reference to the drawings.

Figure 1:
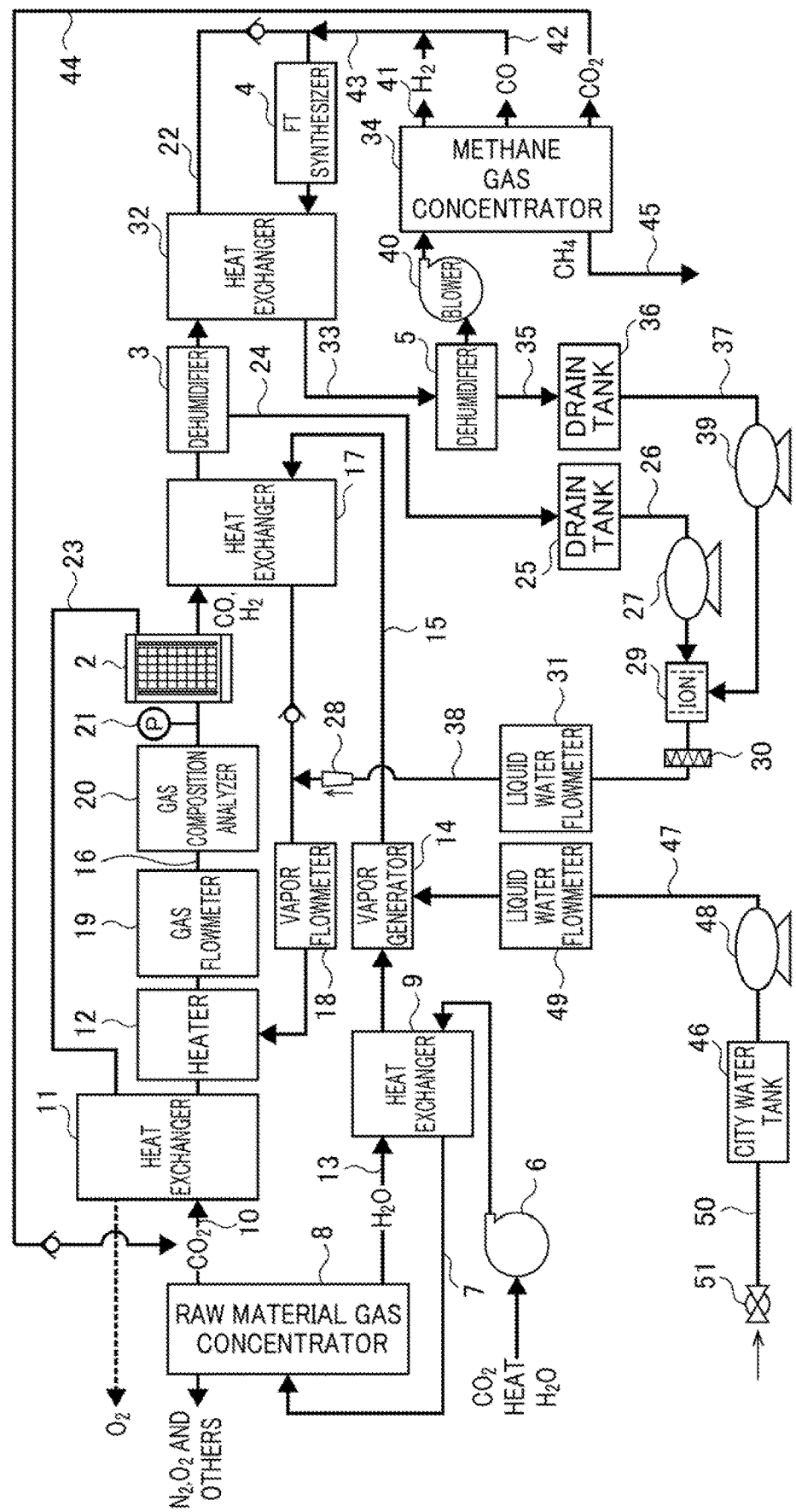
FIG. 1 is a schematic diagram showing a fuel producing system according to an embodiment of the present invention.

FIG. 1 is a schematic diagram showing a fuel producing system according to an embodiment of the present invention. A fuel producing system 1 of the present embodiment includes an electrolyzing unit 2 for electrolyzing a raw material gas containing carbon dioxide and water vapor to generate a product gas containing hydrogen and carbon monoxide, a first gas-liquid separation unit 3 for performing gas-liquid separation on the product gas, a synthesizing unit 4 for producing a synthesis gas containing methane from the product gas from which water has been separated in the first gas-liquid separation unit 3, and a second gas-liquid separation unit 5 for performing gas-liquid separation on the synthesis gas.

The electrolyzing unit 2 has a conventionally known configuration in which the raw material gas is electrolyzed to generate the product gas. Specifically, the electrolyzing unit 2 includes a cathode electrode, an anode electrode, and an oxygen ion permeable membrane provided between the cathode electrode and the anode electrode. With such a configuration, upon application of power between the anode electrode and the cathode electrode, water vapor and carbon dioxide of the raw material gas supplied to the cathode electrode are sequentially electrolyzed, so that the product gas is generated at the cathode electrode. At this time, generated oxygen ions pass through the oxygen ion permeable membrane and move to the anode electrode side. The oxygen ions cause oxygen generation electrode reaction at the anode electrode to generate an oxygen gas.

Raw materials containing carbon dioxide, water, and the like generated in steelworks, garbage disposal facilities, and the like are used as raw materials for the raw material gas to be supplied to the electrolyzing unit 2. The raw material containing carbon dioxide, water and the like is supplied from a storage unit (not shown) to a raw material gas concentrator 8 via a raw material supply path 7 by a pump 6. At this time, the raw material containing carbon dioxide, water and the like is cooled by a heat exchanger 9, and then supplied to the raw material gas concentrator 8. Impurities such as nitrogen and oxygen contained in the raw material are removed in the raw material gas concentrator 8.

Carbon dioxide is supplied from the raw material gas concentrator 8 to the electrolyzing unit 2 via a carbon dioxide supply path 10. At this time, the carbon dioxide is heated in a heat exchanger 11. The carbon dioxide heated in the heat exchanger 11 is further heated in a heater 12 provided in the carbon dioxide supply path 10, and then supplied to the electrolyzing unit 2.

Further, water is supplied from the raw material gas concentrator 8 to a vapor generator 14 via a water supply path 13. At this time, the water is heated in the heat exchanger 9. As described above, the heat exchanger 9 cools the raw materials from the storage unit. In other words, the heat exchanger 9 is an indirect heat exchanger for heat-exchanging the raw materials from the storage unit with the water from the raw material gas concentrator 8 without mixing the raw materials and the water.

The vapor generator 14 changes water into water vapor, for example, it is a boiler. The water vapor from the vapor generator 14 is supplied to the electrolyzing unit 2 via a vapor path 15. In the present embodiment, the vapor path 15 and the carbon dioxide supply path 10 form a common pipeline 16 via the heater 12 on their downstream sides. Therefore, the water vapor from the vapor generator 14 is heated in the heater 12, and then supplied to the electrolyzing unit 2. In the illustrated example, the water vapor from the vapor generator 14 is heated in a heat exchanger 17 before being heated in the heater 12. A vapor flowmeter 18 for measuring the amount of water vapor is provided in the vapor path 15 between the heat exchanger 17 and the heater 12. Note that the common pipeline 16 is provided with a gas flowmeter 19 for measuring the flow rate of gas passing through the common pipeline 16, a gas composition analyzer 20 for analyzing the gas composition of gas passing through the common pipeline 16, and a pressure gauge 21 for measuring the pressure of gas passing through the common pipeline 16.

When the raw material gas containing carbon dioxide and water vapor is supplied to the electrolyzing unit 2, the product gas containing hydrogen and carbon monoxide is generated in the electrolyzing unit 2 as described above. The product gas generated in the electrolyzing unit 2 is supplied to the synthesizing unit 4 described later via a product gas supply path 22. At this time, the product gas is cooled in the heat exchanger 17. As described above, the heat exchanger 17 heats the water vapor from the vapor generator 14. In other words, the heat exchanger 17 is an indirect heat exchanger for heat-exchanging the water vapor from the vapor generator 14 with the product gas from the electrolyzing unit 2 without mixing the water vapor and the product gas. Note that the generated oxygen gas is sent to an oxygen discharge path 23.

The product gas cooled in the heat exchanger 17 is passed through a first gas-liquid separation unit 3 provided in the product gas supply path 22. The first gas-liquid separation unit 3 is, for example, a dehumidifier. The first gas-liquid separation unit 3 performs gas-liquid separation on the product gas generated in the electrolyzing unit 2. In other words, in the first gas-liquid separation unit 3, the product gas is divided into a gas containing hydrogen and carbon monoxide and water that has not reacted in the electrolyzing unit 2.

The water separated in the first gas-liquid separation unit 3 is supplied via a first separated water supply path 24 to a first drain tank 25 and stored there. The separated water from the first drain tank 25 is mixed with the water vapor in the vapor path 15 via a first water supply path 26. In the illustrated example, the first water supply path 26 is connected to the vapor path 15 between the vapor flowmeter 18 and the heat exchanger 17. The first water supply path 26 is provided with a first liquid feeding pump 27 and an injector 28. The injector 28 is provided on the downstream side of the first liquid feeding pump 27. Therefore, the separated water in the first drain tank 25 can be supplied into the vapor path 15 by actuating the first liquid feeding pump 27. The separated water is injected to and mixed with the water vapor in the vapor path 15 via the injector 28. The water vapor mixed with the separated water is heated in the heater 12, and then supplied to the electrolyzing unit 2.

In the present embodiment, the first water supply path 26 is provided with an ion exchange resin unit 29 and a filter 30 between the first liquid feeding pump 27 and the injector 28. The filter 30 is provided on the downstream side of the ion exchange resin unit 29. Therefore, the separated water from the first drain tank 25 sequentially passes through the ion exchange resin unit 29 and the filter 30 before being mixed with the water vapor in the vapor path 15. Cation ions in the separated water are removed in the ion exchange resin unit 29, and dust and the like in the separated water are removed in the filter 30. Note that the first water supply path 26 is provided with a liquid water flowmeter 31 for measuring the flow rate of the separated water between the filter 30 and the injector 28.

Further, the product gas from which water is separated in the first gas-liquid separation unit 3 is heated in a heat exchanger 32, and then supplied to the synthesizing unit 4. The synthesizing unit 4 generates a synthesis gas from the product gas, for example, by Fischer-Tropsch synthesis. Specifically, in the synthesizing unit 4, the product gas from which water has been separated in the first gas-liquid separation unit 3 is passed through a catalyst to generate the synthesis gas. Note that with respect to the catalyst, the present embodiment uses a catalyst for producing methane because it generates a product gas containing methane.

The synthesis gas containing methane produced in the synthesizing unit 4 is supplied to a methane gas concentrator 34 via a synthesis gas supply path 33. At this time, the synthesis gas is cooled in the heat exchanger 32. As described above, the heat exchanger 32 heats the product gas that has passed through the first gas-liquid separation unit 3. In other words, the heat exchanger 32 is an indirect heat exchanger for heat-exchanging the product gas passing through the first gas-liquid separation unit 3 with the synthesis gas from the synthesizing unit 4 without mixing the product gas and the synthesis gas.

The synthesis gas cooled in the heat exchanger 32 is passed through the second gas-liquid separation unit 5. The second gas-liquid separation unit 5 is, for example, a dehumidifier. The second gas-liquid separation unit 5 performs gas-liquid separation on the synthesis gas generated in the synthesizing unit 4. In other words, the synthesis gas is divided into a synthesis gas containing methane and water separated from the synthesis gas in the second gas-liquid separation unit 5.

The water separated in the second gas-liquid separation unit 5 is supplied to a second drain tank 36 via a second separated water supply path 35 and stored there. The separated water from the second drain tank 36 is mixed with the water vapor in the vapor path 15 via a second water supply path 37. In the present embodiment, the first water supply path 26 and the second water supply path 37 forms a common pipeline 38 via the ion exchange resin unit 29 on their downstream side. A second liquid feeding pump 39 is provided in the second water supply path 37 on the upstream side of the common pipeline 38. Therefore, the separated water in the second drain tank 36 can be supplied into the vapor path 15 by actuating the second liquid feeding pump 39. At this time, the separated water in the second drain tank 36 passes through the ion exchange resin unit 29 and the filter 30, and then is injected to and mixed with the water vapor in the vapor path 15 through the injector 28.

Further, the synthesis gas from which water has been separated in the second gas-liquid separation unit 5 is supplied to the methane gas concentrator 34 by a blower 40 provided in the synthesis gas supply path 33. Impurities such as hydrogen, carbon monoxide and carbon dioxide contained in the synthesis gas are removed in the methane gas concentrator 34. The hydrogen removed from the synthesis gas is returned to the product gas supply path 22 via a hydrogen return path 41. The hydrogen return path 41 is connected to the product gas supply path 22 on the downstream side of the heat exchanger 32. The carbon monoxide removed from the synthesis gas is returned to the product gas supply path 22 via a carbon monoxide return path 42. The carbon monoxide return path 42 is connected to the product gas supply path 22 on the downstream side of the heat exchanger 32. In the present embodiment, the hydrogen return path 41 and the carbon monoxide return path 42 form a common pipeline 43 on the downstream sides thereof. The carbon dioxide removed from the synthesis gas is returned to the carbon dioxide supply path 10 via a carbon dioxide return path 44. The carbon dioxide return path 44 is connected to the carbon dioxide supply path 10 on the upstream side of the heat exchanger 11. Further, a methane gas is supplied from the methane gas concentrator 34 via a methane gas discharge path 45 to a storage tank (not shown), and stored there.

Here, the fuel producing system 1 of the present embodiment has a city water tank 46 in which city water is stored. The water in the city water tank 46 is supplied to the water supply path 13 via a water supply path 47. In the illustrated example, the water supply path 47 is connected to the vapor generator 14. A third liquid feeding pump 48 is provided in the water supply path 47. Therefore, the water in the city water tank 46 can be supplied to the vapor generator 14 by actuating the third liquid feeding pump 48. The amount of water to be supplied to the vapor generator 14 is measured by a liquid water flowmeter 49 provided in the water supply path 47 on the downstream side of the third liquid feeding pump 48. The water supplied from the city water tank 46 to the vapor generator 14 is vaporized into water vapor in the vapor generator 14, and supplied to the electrolyzing unit 2 via the vapor path 15. Note that the city water tank 46 is capable of supplying, for example, city water. Therefore, a city water supply path 50 is connected to the city water tank 46. The city water supply path 50 is provided with a city water supply valve 51 for opening and closing the city water supply path 50.

In this way, the fuel producing system 1 of the present embodiment produces the methane gas from the raw material gas containing carbon dioxide and water vapor. At this time, as described above, the water vapor produced from the water separated in the first gas-liquid separation unit 3, and the water vapor produced from the water separated in the second gas-liquid separation unit 5, or the water vapor produced from the water from the city water tank 46 can be supplied to the electrolyzing unit 2 in addition to the raw material gas. Therefore, when the water vapor in the raw material is in short supply, it can be replenished, and the water separated in the first gas-liquid separation unit 3 and the water separated in the second gas-liquid separation unit 5 can be reused. The water separated in the first gas-liquid separation unit 3 and the second gas-liquid separation unit 5 has a large amount of carbon dioxide dissolved therein as compared with the city water.

Figure 2A:
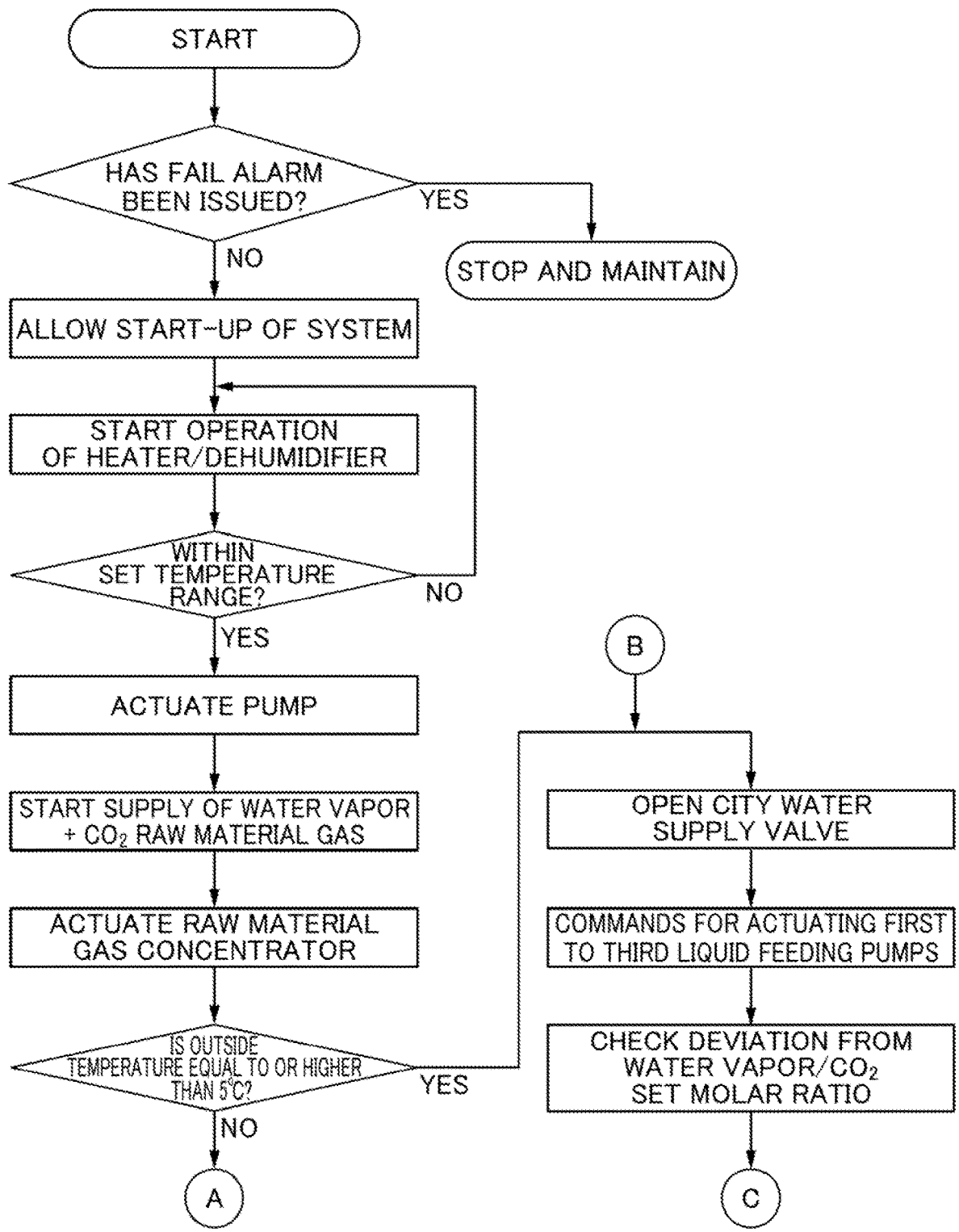
FIG. 2A is a flowchart showing a fuel producing operation of the fuel producing system of FIG. 1.
Figure 2B:
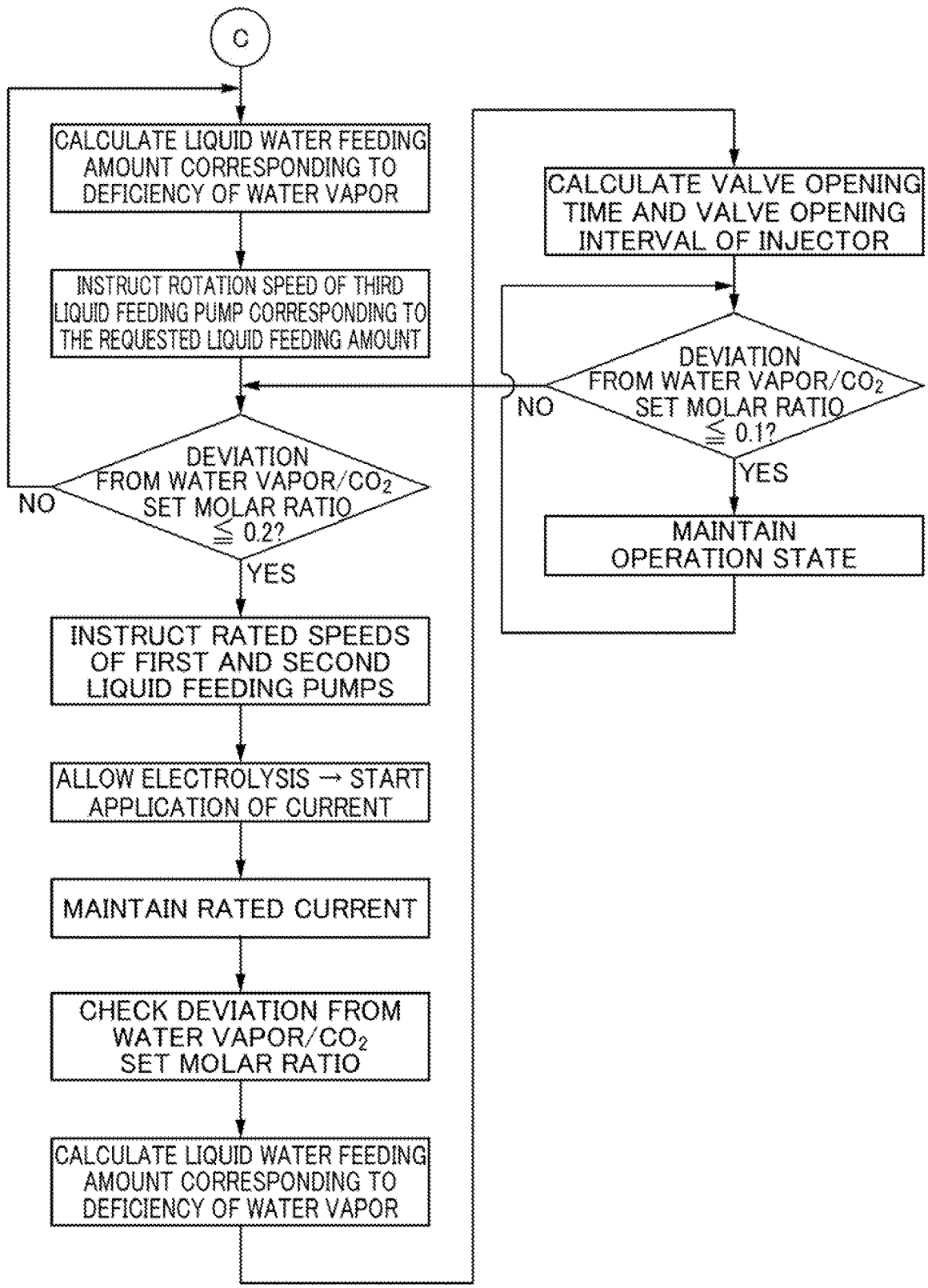
FIG. 2B is a flowchart showing the fuel producing operation of the fuel producing system of FIG. 1.
Figure 3:
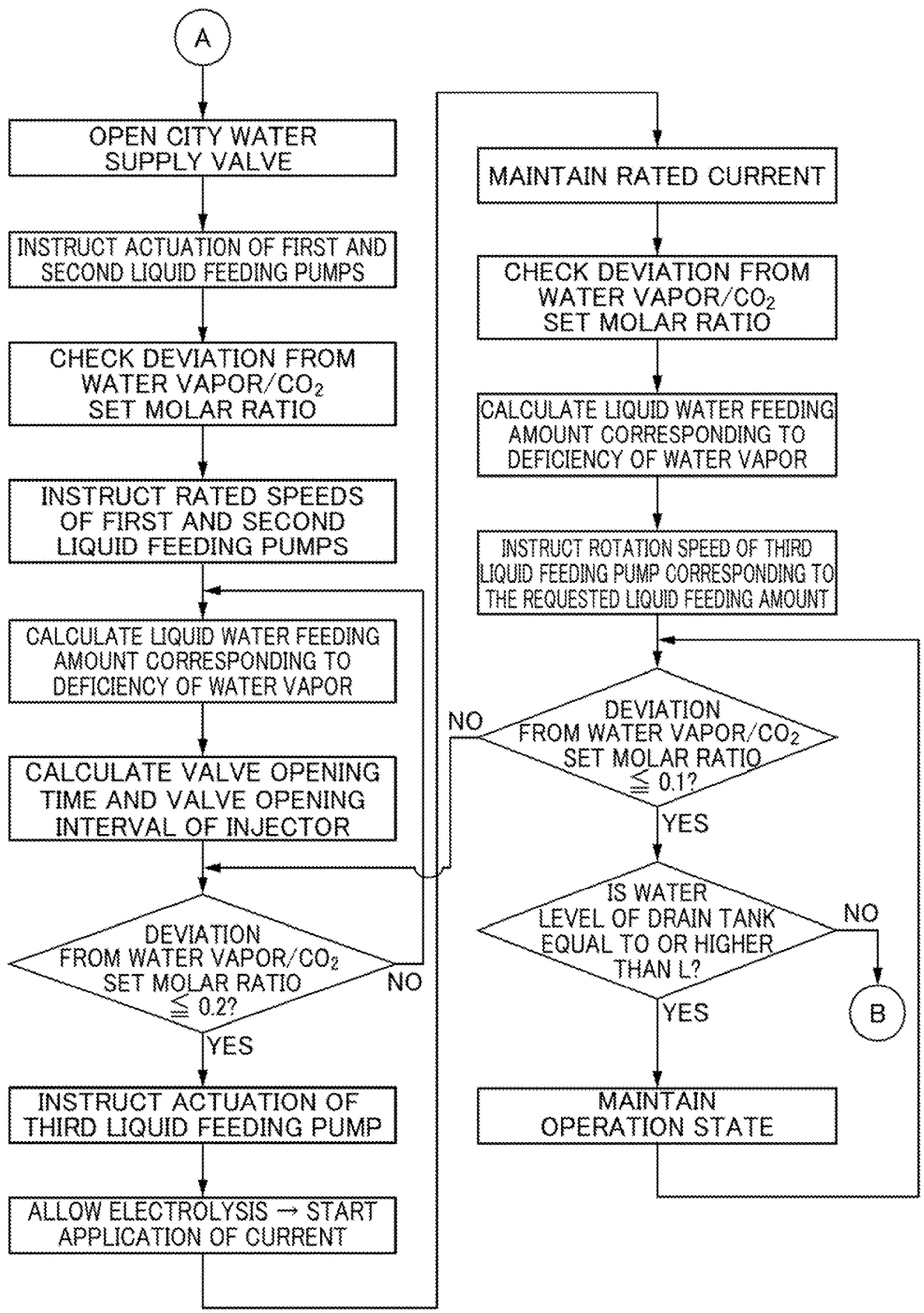
FIG. 3 is a flowchart showing a part of the fuel producing operation of the fuel producing system of FIG. 1.

FIG. 2A and FIG. 2B are flowcharts showing the fuel producing operation of the fuel producing system 1 of the present embodiment. FIG. 3 is a flowchart showing a part of the fuel producing operation of the fuel producing system 1 of the present embodiment. Note that the operation of the fuel producing system 1 of the present embodiment is automatically performed by a controller (not shown).

When the fuel producing system 1 of the present embodiment is operated, it is first confirmed whether or not a fail alarm has been issued. When a fail alarm has been issued, the system is maintained in a stop state. On the other hand, when no fail alarm has been issued, the system is allowed to be actuated. When the system is allowed to be actuated, the operations of the heater 12, the first gas-liquid separation unit 3 and the second gas-liquid separation unit 5 are started. When the heater 12 is operated, the inside of the electrolyzing unit 2 is heated. Then, it is determined whether or not the temperature in the electrolyzing unit 2 is within a set temperature range. When the temperature in the electrolyzing unit 2 is within the set temperature range, the pump 6 is actuated.

When the pump 6 is actuated, supply of the raw material gas containing water vapor and carbon dioxide is started. Specifically, the raw material gas concentrator 8 is actuated. As a result, the raw material from the storage unit is supplied to the raw material gas concentrator 8 to remove impurities such as nitrogen and oxygen. Carbon dioxide discharged from the raw material gas concentrator 8 is supplied to the electrolyzing unit 2 via the carbon dioxide supply path 10. Further, water discharged from the raw material gas concentrator 8 is vaporized into water vapor in the vapor generator 14, and supplied to the electrolyzing unit 2 via the vapor path 15.

After the raw material gas concentrator 8 is actuated, an outside air temperature is determined by outside air temperature determining means. Here, the outside air temperature is an environmental temperature around the electrolyzing unit 2. When the outside air temperature is a predetermined temperature (5° C. in the present embodiment) or higher, a first operation is performed in which water vapor produced from water from the city water tank 46 is supplied to the electrolyzing unit 2 in addition to the raw material gas. Specifically, the city water supply valve 51 is first opened to supply city water into the city water tank 46. Then, a start-up command is given to the first liquid feeding pump 27, the second liquid feeding pump 39, and the third liquid feeding pump 48. After this start-up command is given, the deviation from a set value of the molar ratio of water vapor/carbon dioxide in the raw material gas being supplied to the electrolyzing unit 2 is checked. The molar ratio of water vapor/carbon dioxide in the raw material gas being supplied to the electrolyzing unit 2 is determined by the gas flowmeter 19, the gas composition analyzer 20, and the pressure gauge 21. The difference between the determined value and the set value is the deviation.

Based on the deviation determined as described above, a deficiency of water vapor with respect to carbon dioxide to be supplied to the electrolyzing unit 2 is determined. Then, the amount of water corresponding to this deficiency of water vapor is calculated. Based on this calculated amount of water, the rotation speed of the third liquid feeding pump 48 is instructed. In other words, water corresponding to the insufficient amount of water vapor is supplied from the city water tank 46 to the vapor generator 14.

Thereafter, it is determined whether or not the deviation from the set value of the molar ratio of water vapor/carbon dioxide in the raw material gas to be supplied to the electrolyzing unit 2 is equal to or less than a predetermined value (0.2 or less in the present embodiment). When the deviation is equal to or less than the predetermined value, the operation is performed as follows. Specifically, when the deviation from the set value of the molar ratio of water vapor/carbon dioxide in the raw material gas becomes equal to or less than the predetermined value during the first operation described above, a fourth operation is performed in which in addition to the supply of water vapor produced from water from the city water tank 46 as a water supply source, water vapor produced from water separated in the first gas-liquid separation unit 3 and water vapor produced from water separated in the second gas-liquid separation unit 5 are supplied to the electrolyzing unit 2 in addition to the raw material gas.

When the fourth operation is performed, first, the third liquid feeding pump 48 is continuously operated to continue the supply of water from the city water tank 46 to the vapor generator 14. Thereafter, rated speed commands for the first liquid feeding pump 27 and the second liquid feeding pump 39 are given. Then, electrolysis in the electrolyzing unit 2 is allowed. In other words, current is applied so that electrolysis is performed in the electrolyzing unit 2. After the current is applied, a rated current is maintained. The deviation from the set value of the molar ratio of water vapor/carbon dioxide in the raw material gas being supplied to the electrolyzing unit 2 is checked while the rated current is being maintained. Based on this deviation, a deficiency of water vapor with respect to carbon dioxide to be supplied to the electrolyzing unit 2 is determined. The amount of water corresponding to this deficiency of water vapor is calculated. Based on this calculated amount of water, a valve opening time and a valve opening interval of the injector 28 are calculated. At the determined valve opening time and the valve opening interval of the injector 28, water is injected and supplied from the first drain tank 25 and the second drain tank 36 to the water vapor in the vapor path 15 via the injector 28.

It is determined whether or not the deviation from the set value of the molar ratio of water vapor/carbon dioxide in the raw material gas being supplied to the electrolyzing unit 2 is equal to or less than a predetermined value (0.1 or less in the present embodiment) while the water from the first drain tank 25 and the second drain tank 36 is being injected and supplied to the water vapor in the vapor path 15. When the deviation is equal to or less than the predetermined value, the operation state is maintained. On the other hand, when the deviation is larger than the predetermined value, the above-mentioned fourth operation is performed.

Next, a case where the outside air temperature is lower than the predetermined temperature (5° C. in the present embodiment) will be described. When the outside air temperature is lower than the predetermined temperature, the water separated in the first gas-liquid separation unit 3 and the second gas-liquid separation unit 5 is positively used. This is because more carbon dioxide is dissolved in the water than that in city water, and the molar ratio of water vapor/carbon dioxide can be adjusted with a smaller flow rate as compared with a case where city water is supplied. Therefore, as compared with the case where city water is supplied, it is possible to supply water vapor and carbon dioxide which have been heated and adjusted by the heater 12, so that the apparatus can be shifted from the start-up to the normal operation earlier. In this case, a second operation is performed in which the water vapor produced from the water separated in the first gas-liquid separation unit 3 and the water vapor produced from the water separated in the second gas-liquid separation unit 5 are supplied to the electrolyzing unit 2 in addition to the raw material gas. Specifically, first, the city water supply valve 51 is opened to supply city water into the city water tank 46. Then, a start-up command is given to the first liquid feeding pump 27 and the second liquid feeding pump 39. After this start-up command is given, the deviation from the set value of the molar ratio of water vapor/carbon dioxide in the raw material gas being supplied to the electrolyzing unit 2 is checked.

After checking the deviation, the rated speed commands for the first liquid feeding pump 27 and the second liquid feeding pump 39 are given. A deficiency of water vapor with respect to carbon dioxide to be supplied to the electrolyzing unit 2 is determined based on the earlier checked deviation. Then, the amount of water corresponding to this deficiency of water vapor is calculated. The valve opening time and the valve opening interval of the injector 28 are calculated based on this calculated amount of water. At the determined valve opening time and the valve opening interval of the injector 28, water is injected and supplied from the first drain tank 25 and the second drain tank 36 into the water vapor in the vapor path 15 via the injector 28.

It is determined whether or not the deviation from the set value of the molar ratio of water vapor/carbon dioxide in the raw material gas being supplied to the electrolyzing unit 2 is equal to or less than a predetermined value (0.2 or less in the present embodiment) while the water from the first drain tank 25 and the second drain tank 36 are being injected and supplied to the water vapor in the vapor path 15. When the deviation is equal to or less than the predetermined value, the operation is performed as follows. Specifically, when the deviation from the set value of the molar ratio of water vapor/carbon dioxide in the raw material gas becomes equal to or less than the predetermined value during the above-mentioned second operation, a third operation is performed in which in addition to supply of water vapor produced from water separated in the first gas-liquid separation unit 3 and water vapor produced from water separated in the second gas-liquid separation unit 5, water vapor produced from water from the water supply source is supplied to the electrolyzing unit 2 in addition to the raw material gas.

When performing the third operation, the operations of the first liquid feeding pump 27 and the second liquid feeding pump 39 are continued to continue the water supply from the first drain tank 25 and the second drain tank 36. Thereafter, a start-up command for the third liquid feeding pump 48 is given. Then, electrolysis in the electrolyzing unit 2 is allowed. In other words, current is applied so that electrolysis is performed in the electrolyzing unit 2. After the current is applied, the rated current is maintained. While the rated current is being maintained, the deviation from the set value of the molar ratio of water vapor/carbon dioxide in the raw material gas being supplied to the electrolyzing unit 2 is checked. Based on this deviation, a deficiency of water vapor with respect to carbon dioxide to be supplied to the electrolyzing unit 2 is determined. Then, the amount of water corresponding to this deficiency of water vapor is calculated. Based on this calculated amount of water, the rotation speed of the third liquid feeding pump 48 is instructed. In other words, water corresponding to the deficiency of water vapor is supplied from the city water tank 46 to the vapor generator 14.

It is determined whether or not the deviation from the set value of the molar ratio of water vapor/carbon dioxide in the raw material gas being supplied to the electrolyzing unit 2 is equal to or less than a predetermined value (0.1 or less in the present embodiment) while water vapor produced from water from the city water tank 46 is supplied. When the deviation is larger than the predetermined value, the above-mentioned third operation is performed. On the other hand, when the deviation is equal to or less than the predetermined value, it is determined whether or not the water levels of the first drain tank 25 and the second drain tank 36 are equal to or higher than a set water level L. When they are equal to or higher than the set water level L, the operating state is maintained. On the other hand, when they are lower than the set water level L, the operation is performed as follows. Specifically, when the water level in the first drain tank 25 in which water separated in the first gas-liquid separation unit 3 is stored, and the water level in the second drain tank 36 in which water separated in the second gas-liquid separation unit 5 is stored are lower than the set water level during the third operation described above, water vapor produced from water from the water supply source is supplied to the electrolyzing unit 2 in addition to the raw material gas, and the supply of water vapor produced from water separated in the first gas-liquid separation unit 3 and water vapor produced from water separated in the second gas-liquid separation unit 5 is stopped. In short, the operation is returned to the first operation described above.

Figure 4A:
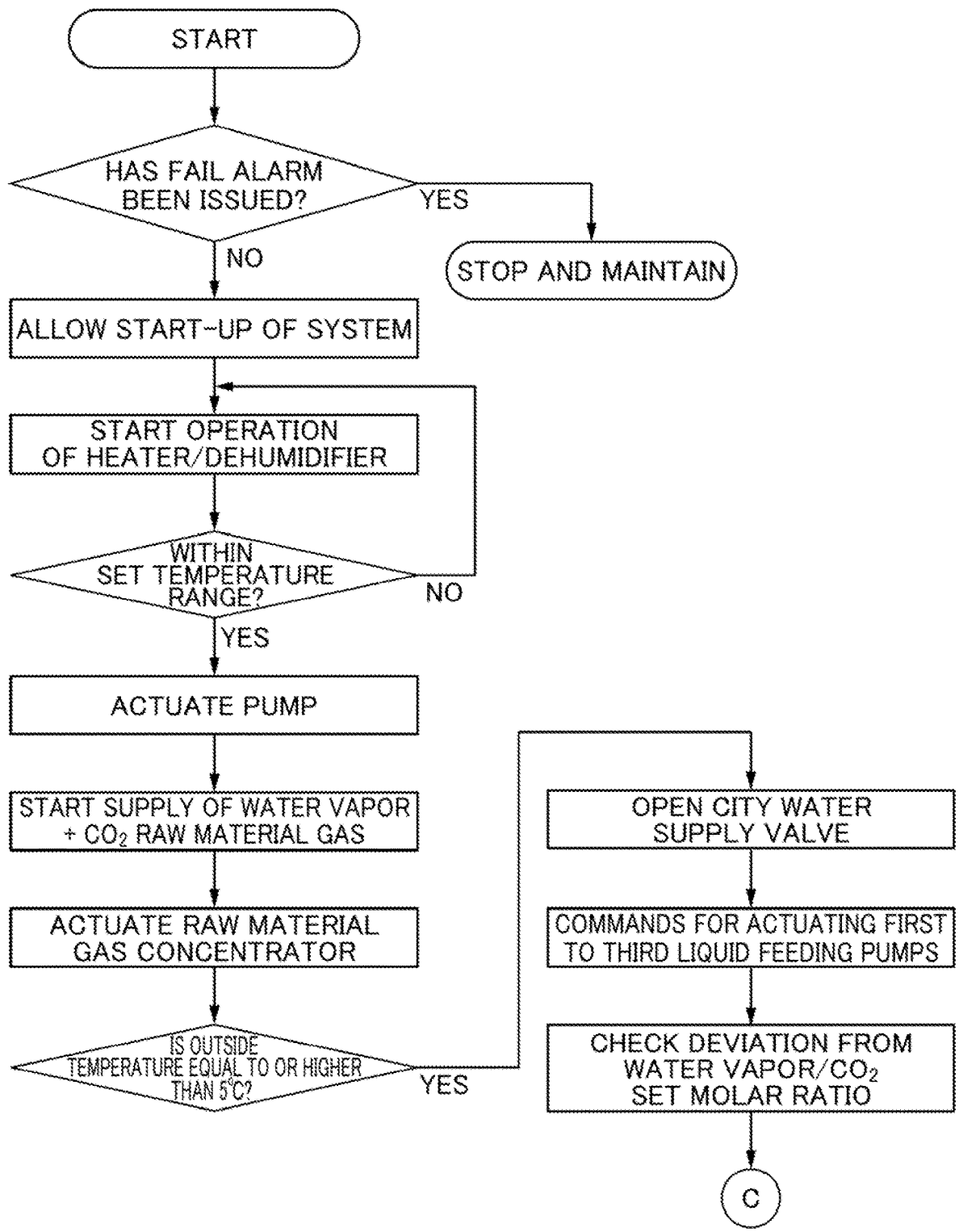
FIG. 4A is a flowchart showing another fuel producing operation of the fuel producing system of FIG. 1.
Figure 4B:
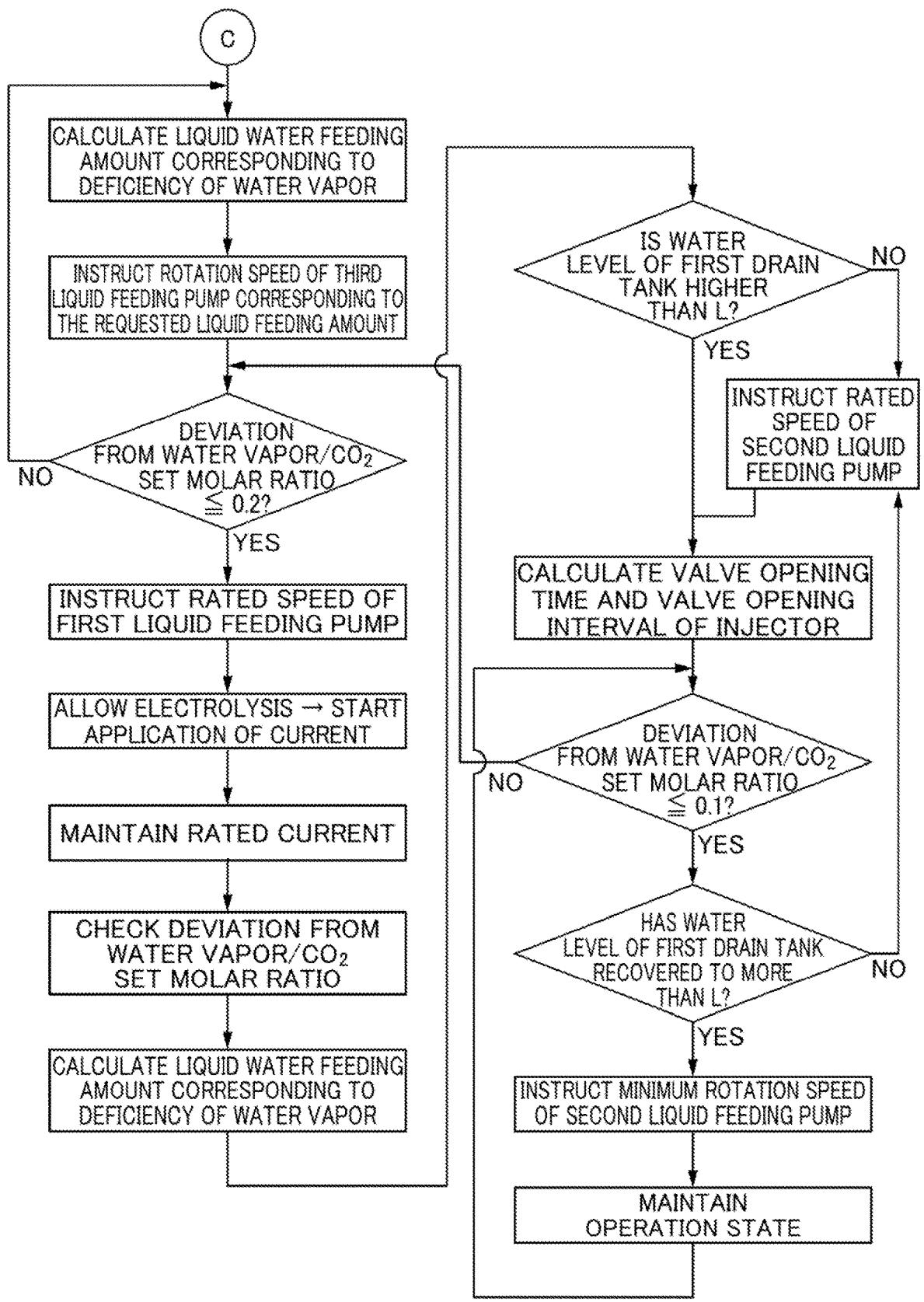
FIG. 4B is a flowchart showing another fuel producing operation of the fuel producing system of FIG. 1.

FIG. 4A and FIG. 4B are flowcharts showing another fuel producing operation of the fuel producing system 1 of the present embodiment. Note that in the fuel producing operation of this case, the characteristic portions thereof will be described, and the description of the matters described with respect to FIG. 2A, FIG. 2B and FIG. 3 will be omitted. Further, as in the case of FIG. 2A, FIG. 2B and FIG. 3, the operation of the fuel producing system 1 of FIG. 4A and FIG. 4B is also automatically performed by a controller (not shown).

In the operation shown in FIG. 4A and FIG. 4B, during the first operation described above, it is determined whether or not the deviation from the set value of the molar ratio of water vapor/carbon dioxide in the raw material gas being supplied to the electrolyzing unit 2 is equal to or less than a predetermined value (0.2 or less in the present embodiment) as shown in FIG. 4B. When the deviation is equal to or less than the predetermined value, the third liquid feeding pump 48 is continuously operated, and the rated speed command for the first liquid feeding pump 27 is given. Then, electrolysis in the electrolyzing unit 2 is allowed. In other words, current is applied so that electrolysis is performed in the electrolyzing unit 2. After the current is applied, a rated current is maintained. The deviation from the set value of the molar ratio of water vapor/carbon dioxide in the raw material gas being supplied to the electrolyzing unit 2 is checked while the rated current is being maintained. Based on this deviation, a deficiency of water vapor with respect to carbon dioxide to be supplied to the electrolyzing unit 2 is determined. Then, the amount of water corresponding to this deficiency of water vapor is calculated.

Thereafter, it is determined whether or not the water level of the first drain tank 25 is equal to or higher than the set water level L. When the water level is equal to or higher than the set water level L, the valve opening time and the valve opening interval of the injector 28 are calculated based on the earlier calculated water amount. At the determined valve opening time and the valve opening interval of the injector 28, water is injected and supplied from the first drain tank 25 to the water vapor in the vapor path 15 via the injector 28. On the other hand, when the water level is lower than the set water level L, a rated speed command for the second liquid feeding pump 39 is given. Then, at the earlier determined valve opening time and the valve opening interval of the injector 28, water is injected and supplied from the first drain tank 25 and the second drain tank 36 to the water vapor in the vapor path 15 via the injector 28.

It is determined whether or not the deviation from the set value of the molar ratio of water vapor/carbon dioxide in the raw material gas being supplied to the electrolyzing unit 2 is equal to or less than a predetermined value (0.1 or less in the present embodiment) during the injection and supply of the water from the first drain tank 25 to the water vapor in the vapor path 15, or during the injection and supply of the water from the first drain tank 25 and the second drain tank 36 to the water vapor in the vapor path 15. When the deviation is larger than the predetermined value, as shown in FIG. 4B, the processing is returned to a step of determining whether or not the deviation from the set value of the molar ratio of water vapor/carbon dioxide in the raw material gas being supplied to the electrolyzing unit 2 is equal to or less than the predetermined value (0.2 or less in the present embodiment). On the other hand, when the deviation is equal to or less than the predetermined value, it is determined whether or not the water level of the first drain tank 25 has become higher than the set water level L. When the water level has not become higher than the set water level L, the processing is returned to a step of giving the rated speed command for the second liquid feeding pump 39. On the other hand, when the water level of the first drain tank 25 has become higher than the set water level L, a minimum rotation speed command for the second liquid feeding pump 39 is given, and the operation state is maintained.

Note that the present invention is not limited to the above embodiment, and modifications and improvements within the range in which the object of the present invention can be achieved are included in the present invention.

For example, in the above embodiment, the first gas-liquid separation unit 3 and the second gas-liquid separation unit 5 are dehumidifiers, but the present invention is not limited to the dehumidifier, and any device can be used insofar as it can perform gas-liquid separation.

EXPLANATION OF REFERENCE NUMERALS

1: Fuel producing system
2: Electrolyzing unit
3: First gas-liquid separation unit
4: Synthesizing unit
5: Second gas-liquid separation unit
25: First drain tank
36: Second drain tank
46: City water tank

What is claimed is:

1. A fuel producing system comprising:
a raw material gas concentrator that is supplied with a raw material containing carbon dioxide and water and removes impurities contained in the raw material;
a heat exchanger that heat-exchanges the raw material supplied to the raw material gas concentrator with water from the raw material gas concentrator to heat the water from the raw material gas concentrator;
a vapor generator that changes water heated by the heat exchanger that heats the water from the raw material gas concentrator, into water vapor;
an electrolyzer that is supplied with a raw material gas containing carbon dioxide from the raw material gas concentrator and water vapor from the vapor generator, and electrolyzes the raw material gas to generate a product gas containing hydrogen and carbon monoxide;
a first gas-liquid separator that performs gas-liquid separation on the product gas generated in the electrolyzer, to divide the product gas into a gas containing hydrogen and carbon monoxide and water that has not reacted in the electrolyzer;
a heat exchanger that heat-exchanges water vapor supplied from the vapor generator to the electrolyzer with the product gas from the electrolyzer to heat the water vapor supplied from the vapor generator;
a synthesizer that generates a synthesis gas by passing, through a catalyst the product gas from which water has been separated in the first gas-liquid separator, the synthesis gas containing methane;
a second gas-liquid separator that performs gas-liquid separation on the synthesis gas generated in the synthesizer to divide the synthesis gas into a synthesis gas containing methane and water separated from the synthesis gas; and
an injector that injects water separated in the first gas-liquid separator and water separated in the second gas-liquid separator into, and mixes them with, water vapor heated by the heat exchanger that heats water vapor supplied from the vapor generator to the electrolyzer
wherein water vapor produced from water separated in the first gas-liquid separator and injected by the injector and water vapor produced from water separated in the second gas-liquid separator and injected by the injector, or water vapor produced from water from a water supply source are/is allowed to be supplied to the electrolyzer in addition to the raw material gas.

2. The fuel producing system according to claim 1, wherein when an outside air temperature is equal to or higher than a predetermined temperature, a first operation is performed in which water vapor produced from water from the water supply source is supplied to the electrolyzer in addition to the raw material gas, and
wherein when the outside air temperature is lower than the predetermined temperature, a second operation is performed in which water vapor produced from water separated in the first gas-liquid separator and injected by the injector and water vapor produced from water separated in the second gas-liquid separator and injected by the injector are supplied to the electrolyzer in addition to the raw material gas.

3. The fuel producing system according to claim 2, wherein when a deviation from a set value of a molar ratio of water vapor/carbon dioxide in the raw material gas becomes equal to or less than a predetermined value during the second operation, a third operation is performed in which in addition to the raw material gas, water vapor produced from water separated in the first gas-liquid separator and injected by the injector and water vapor produced from water separated in the second gas-liquid separator and injected by the injector, water vapor produced from water from the water supply source is supplied to the electrolyzer.

4. The fuel producing system according to claim 3, wherein when a water level in a first drain tank in which water separated in the first gas-liquid separator is stored, and a water level in a second drain tank in which water separated in the second gas-liquid separator is stored are lower than a set water level during the third operation, water vapor produced from water from the water supply source is supplied to the electrolyzer in addition to the raw material gas, and supply of water vapor produced from water separated in the first gas-liquid separator and injected by the injector and water vapor produced from water separated in the second gas-liquid separator and injected by the injector is stopped.

5. The fuel producing system according to claim 2, wherein when a deviation from a set value of a molar ratio of water vapor/carbon dioxide in the raw material gas becomes equal to or less than a predetermined value during the first operation, a fourth operation is performed in which in addition to the raw material gas and water vapor produced from water from the water supply source, water vapor produced from water separated in the first gas-liquid separator and injected by the injector and water vapor produced from water separated in the second gas-liquid separator and injected by the injector are supplied to the electrolyzer.

* * * * *